United States Patent
Needhan et al.

(10) Patent No.: US 8,448,846 B2
(45) Date of Patent: May 28, 2013

(54) MEDICATION RECORDING DEVICE

(75) Inventors: Bradford H. Needhan, North Plains, OR (US); Kevin Rhodes, Beaverton, OR (US)

(73) Assignee: Intel-GE Care Innovations LLC, Roseville, CA (US)

(*) Notice: Subject to any disclaimer, the term of this patent is extended or adjusted under 35 U.S.C. 154(b) by 929 days.

(21) Appl. No.: 11/941,959

(22) Filed: Nov. 18, 2007

(65) Prior Publication Data
US 2009/0127339 A1   May 21, 2009

(51) Int. Cl.
*G06F 17/00* (2006.01)

(52) U.S. Cl.
USPC ............. 235/375; 235/487; 705/2; 705/3

(58) Field of Classification Search
USPC .......... 235/375, 454, 462.14, 462.45, 462.49, 235/472.01–472.03, 487; 705/2, 3
See application file for complete search history.

(56) References Cited

U.S. PATENT DOCUMENTS

| | | | |
|---|---|---|---|
| 5,408,443 A | | 4/1995 | Weinberger |
| 5,752,235 A | | 5/1998 | Kehr |
| 5,845,264 A | * | 12/1998 | Nellhaus ................. 705/28 |
| 2002/0026330 A1 | * | 2/2002 | Klein ..................... 705/3 |
| 2004/0172283 A1 | * | 9/2004 | Vanderveen et al. ....... 705/2 |
| 2006/0169773 A1 | * | 8/2006 | Lyons et al. ............ 235/385 |
| 2007/0294105 A1 | * | 12/2007 | Pierce .................. 705/2 |
| 2008/0177568 A1 | * | 7/2008 | Kotidis ................. 705/2 |
| 2009/0048871 A1 | * | 2/2009 | Skomra ................. 705/3 |

OTHER PUBLICATIONS

Lundell, Jay "Why Elders Forget to Take Their Meds: A Probe Study to Inform a Smart Reminding System", Smart Homes and Beyond, IOS Press, 2006, pp. 98-105.
Labhard, Michael E., "Intelligent Medtracker", U.S. Appl. No. 11/771,339, filed Jun. 29, 2007.
Kimel, Janna C., et al., "Mobile Medication". U.S. Appl. No. 11/644,016, filed Dec. 22, 2006.
Dishongh, Terrance J., "Contextual Medication Prompting Pillbox", U.S. Appl. No. 11/644,017, filed Dec. 22, 2006.
Poisner, David I "Method for Identifying Pills via an Optical Device", U.S. Appl. No. 11/477,676, filed Jun. 30, 2006.

* cited by examiner

*Primary Examiner* — Tuyen K Vo
(74) *Attorney, Agent, or Firm* — Pillsbury Winthrop Shaw Pittman LLP

(57) ABSTRACT

A device and method records and identifies a medication that is to be introduced into a body by generating an image of the medication. The image of the medication is converted to image data of the medication that comprises a format for comparison with medication identification data stored in a database. Time-stamp data is generated and associated with the image data of the medication. The image data of the medication and associated time-stamp data are stored. The medication is identified by comparing one or more medication-identification parameters stored in the database with the image data of the medication.

21 Claims, 2 Drawing Sheets

MEDICATION RECORDING DEVICE

BACKGROUND

In today's society, a large percentage of the human and animal population depend on medication for a variety of reasons. Medication may be delivered in a variety of ways, such as, in bottles, blister packs, daily dose packs, nasal mists, inhalers, eye drops, injections and/or in transdermal patches. These different collections of medications may be received from a pharmacy, over the internet or even over the counter. Many medications require a prescription, however, many medications are available over-the-counter without a prescription.

Those who regularly take or administer medication often create systems to remind themselves of when to administer a dose of medication either to themselves, a pet or someone in their care. For many people, memory aids help keep track of dosing such as, for instance; seven-day medication reminder boxes that record the time the pill was removed from the box, blister packs that record the time the pill was removed from the package and/or medication reminding systems that perform timer or alarm functions issuing reminders when it is time for a person to take or administer a medication.

DETAILED DESCRIPTION

In the following detailed description, numerous specific details are set forth in order to provide a thorough understanding of claimed subject matter. It will, however, be understood by those skilled in the art that claimed subject matter may be practiced without these specific details. In other instances, well-known methods, procedures, and components have not been described in detail so as not to obscure claimed subject matter.

The term 'medication' is used throughout the following disclosure and is intended to refer to any substance used for treatment, control and/or prevention of any human or animal condition, such as, for instance; prevention of disease and/or injury, healing or control of disease and/or injury and/or controlling pain, and claimed subject matter is not limited in this regard. The phrase 'introduced into the body' is used throughout the following disclosure and is intended to refer to delivery of medication into a human or animal body by any of a number of routes, such as for instance; orally, intravenously, intramuscularly, intrathecally, subcutaneously, sublingually, ocularly, nasally, inhalation, cutaneously, and/or transdermally and claimed subject matter is not limited in this regard. The term 'contraindication' is used throughout the following disclosure and is intended to mean one or more factors that render the administration of a medication or the carrying out of a medical procedure inadvisable.

Figure 1:
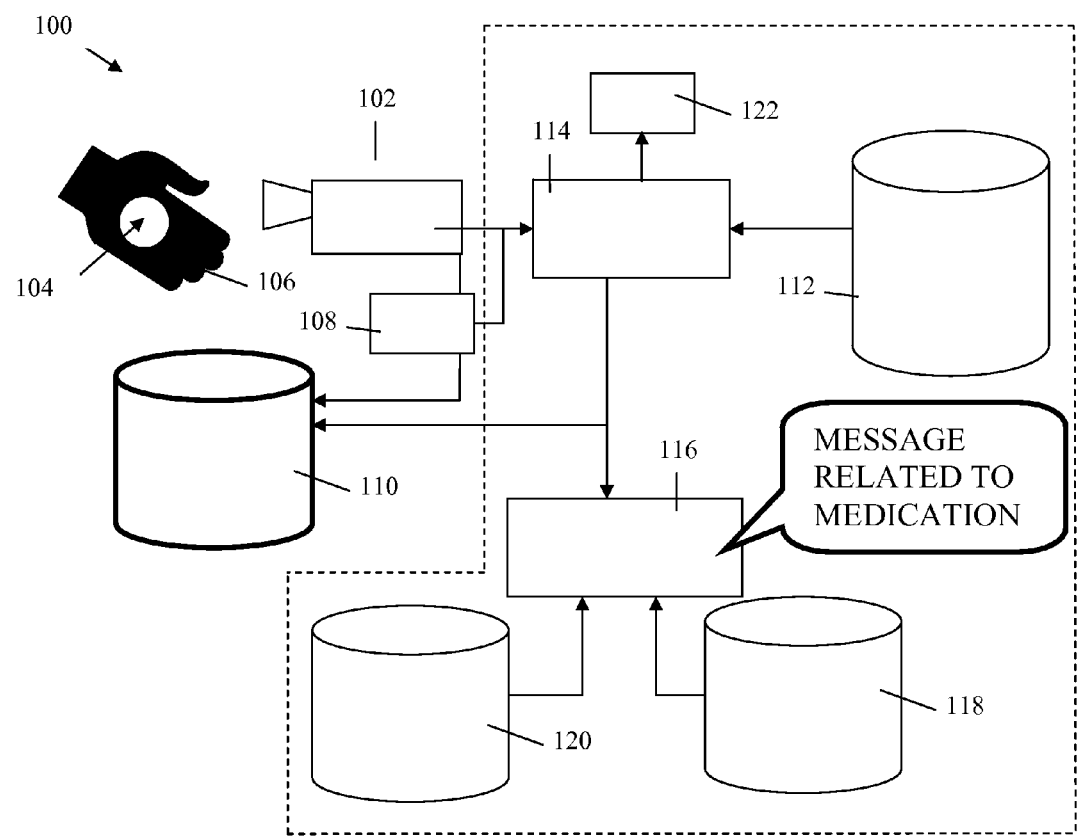
FIG. 1 is a block diagram illustrating a particular embodiment of a medication recording device.

FIG. 1 is a block diagram of a particular embodiment of medication-recording device 100. In a particular embodiment, medication-recording device 100 may comprise imaging device 102 capable of capturing an image of medication 104 to be introduced into a human or animal body and converting the image to image data for medication identification. Such image data for medication identification may comprise data capable of enabling identification of medication. Identification may be by comparison of converted image data with data in a medication-identification database. Such converted image data may comprise any compatible format for comparison with medication-identification database data, such as, a cropped version of the image captured, character string, outline coordinates, color coordinates, bar code data, character data and/or a predetermined image-file format.

In a particular embodiment, medication 104 may be held in a hand 106 of a user when imaging device 102 is capturing the image or medication 104 may stand alone when imaging device 102 captures the image. In a particular embodiment, when a user is about to take, apply and/or administer a medication, the user may hold medication 104 in their open hand, in front of imaging device 102 and capture an image of medication 104. Activating imaging device 102 to capture an image may be done by a variety of methods, such as; by depressing an activating button, touching a touch screen, activating a motion detector, issuing voice commands, and/or through video processing to detect when a hand is poised for image capture and claimed subject matter is not so limited.

According to a particular embodiment, medication 104 may comprise any of a variety of forms, such as, for instance, pills, liquids, mists, inhalants, drops and/or transdermal patches. In a particular embodiment, a user may capture an image of medication 104 in any form, for instance, in liquid or pill form, liquid in an applicator, an inhaler, package, transdermal patch and/or medication bottle. According to a particular embodiment, various medication forms may have markings, colors, sizes, bar codes and/or other characteristics that may serve as identifiers that may enable human recognition or identification of medication 104 from the image. These are, however, merely examples of forms and identifiers a medication may comprise and claimed subject matter is not so limited.

In a particular embodiment, imaging device 102 may comprise any of a variety of devices capable of capturing an image, such as, a traditional camera, a digital camera, an infrared camera, a copier, and/or scanner and claimed subject matter is not limited in this regard. In a particular embodiment, time-stamp unit 108 may be coupled to imaging device 102 and may generate a time stamp. According to a particular embodiment, an image of medication 104 may be associated with a time stamp. In a particular embodiment, processor 114 may associate a time stamp with an image or image data generated by imaging device 102. In another embodiment time-stamp unit 108 may associate a time stamp with an image of medication 104. According to a particular embodiment, time-stamp unit 108 may be coupled to imaging device 102 and processor 114. According to a particular embodiment, an image or image data of medication 104 and the associated time stamp may be stored in non-volatile memory unit 110 which may provide a record of what medications a user has administered, taken, applied or otherwise ingested and when those mediations were administered, taken, applied or otherwise ingested. Such a record may be useful in maintaining a medicinal regimen for humans and/or animals and claimed subject matter is not limited in this regard. In a particular embodiment, such a record may be used by medical personnel or caregivers to enable accurate record keeping of another's medicinal regimen. In a particular embodiment, a record may be reviewed by one's prescriber to either reinforce the instructions to the patient or to adjust the prescription. In the event of an emergency such a record may be valuable diagnostic tool for emergency worker and other medical personnel.

In a particular embodiment, medication-recording device 100 may be capable of identifying medication 104. In a particular embodiment, processor 114 may be capable of accessing medication-identification database 112. Medication-identification database 112 may comprise medication-identification parameters. In a particular embodiment, processor 114 may be capable of identifying medication 104 based at least in part on comparing medication-identification parameters with the image data of the medication 104 image. According to a particular embodiment, user interface 116 may be coupled to processor 114 and may be capable of communicating a message related to identification of the medication. In a particular embodiment, user interface 116 may comprise a variety of interfaces, such as, for instance; a digital display, an audio output, physical output, tactile output and/or other sensory output and claimed subject matter is not limited in this regard. User interface 116 may display a message describing medication 104, for instance, by digital display, audio output and/or tactile readout (such as brail). In another embodiment, user interface 116 may simply issue a tone, alarm and/or vibration to indicate that medication 104 has or has not been identified.

In a particular embodiment, medication-recording device 100 may be capable of verifying that a user is about to take, use, apply and/or administer an approved medication in keeping with a recommended medication regimen. In a particular embodiment, processor 114 may be capable of accessing recommended-medication-regimen database 118. Recommended-medication-regimen database 118 may comprise recommended-medication-regimen parameters. Such parameters may comprise, kind of medication and timing parameters. An increasing number of chronic conditions require the doctor to frequently adjust the patient's dosages, sometimes giving verbal instructions instead of writing a new prescription (e.g., "take your blood pressure pill once every other day now instead of every day"), increasing the chances of a medication-taking error. Medication-regimen database 118 may be accessible to medical advising personnel such that when adjustments to a medication regimen are made they may be entered into medication-regimen database 118 thereby reinforcing the new instructions and reducing medication-taking error.

In a particular embodiment, processor 114 may be capable of verifying that the person is about to take, use, apply and/or administer an approved medication in keeping with a recommended medication regimen based at least in part on comparing recommended-medication-regimen parameters with identified medication 104 and time stamp data of medication 104 image. According to a particular embodiment, user interface 116 may be coupled to processor 114 and may be capable of communicating a message related to verification of conformance to recommended medication regimen. User interface 116 may communicate such a verification message by digital display, audio output and/or tactile readout (such as brail). For example, user interface 116 may say "it's not time yet to take the yellow pills" or "Remember, your doctor told you to only take one of the red pills now." In another embodiment, user interface 116 may simply issue a tone, alarm and/or vibration to indicate that medication 104 is or is not in compliance with a recommended medication regimen.

In a particular embodiment, medication recording device 100 may be capable of determining whether a user is about to take, use, apply and/or administer a contraindicated medication. In a particular embodiment, processor 114 may be capable of accessing medication-contraindication database 120. Medication-contraindication database 120 may comprise medication-contraindication parameters. Such parameters may comprise medication parameters, timing parameters and/or behavioral parameters. In a particular embodiment, a user may be able to input information related to a variety of behavioral variables such as, for instance, whether the individual who is to be administered medication 104 has eaten, exercised, will be driving or has ingested any alcoholic beverage and claimed subject matter is not so limited. According to a particular embodiment, medication-recording device 100 may be capable of receiving behavioral variable data from a variety of sources such as physical input by a user, communication from a diagnostic instrument such as blood-sugar gauges, blood-pressure and heart-rate monitors and/or breath analyzers and claimed subject matter is not limited in this respect. In a particular embodiment, processor 114 may be capable of determining that the person is about to take, use, apply and/or administer a contraindicated medication based at least in part on comparing medication-contraindication parameters with identified medication 104, time-stamp data of medication 104 image and/or any behavioral data.

According to a particular embodiment, user interface 116 may be coupled to processor 114 and may be capable of communicating a message related to whether medication 104 is contraindicated. User interface 116 may communicate such a contraindication message by digital display, audio output and/or tactile readout (such as Braille). For example, user interface 116 may say, "Because you are taking a cold remedy right now, you shouldn't take the blue pill." In another embodiment, user interface 116 may simply issue a tone, alarm and/or vibration to indicate that medication 104 is or is not contraindicated.

In a particular embodiment, medication-recording device 100 may include hand-recognition software capable of identifying the individual whose hand appears in the image, in order to infer whether the patient or one of their caregivers are administering medication 104. In a particular embodiment, medication recording device 100 may be implemented in a cell phone comprising a high-resolution camera, speaker, microphone, and network connectivity to provide a mobile medication-taking record. According to a particular embodiment, each time the person is about to take a pill, they hold the pill in front of their cell-phone camera and take a picture.

In a particular embodiment, medication recording device 100 may comprise transmitter 122 which may be capable of wirelessly transmitting medication information received from processor 114. In a particular embodiment, processor 114 may be capable of converting medication information into data suitable for wireless transmission. In a particular embodiment, transmitter 122 may communicate medication information to a variety of receiving stations such as, for instance, a router connected to the Internet, a wireless receiver connected to a medic alert system and/or a local or on-site receiver capable of communicating medication information to caregivers such as in an assisted care facility and claimed subject matter is not limited in this regard. According to a particular embodiment, transmitter 122 may communicate a variety of medication related messages such as, simply identifying medication, indicating whether a person is following a medication regimen and/or identify medication contraindications and claimed and claimed subject matter is not limited in this regard.

Figure 2:
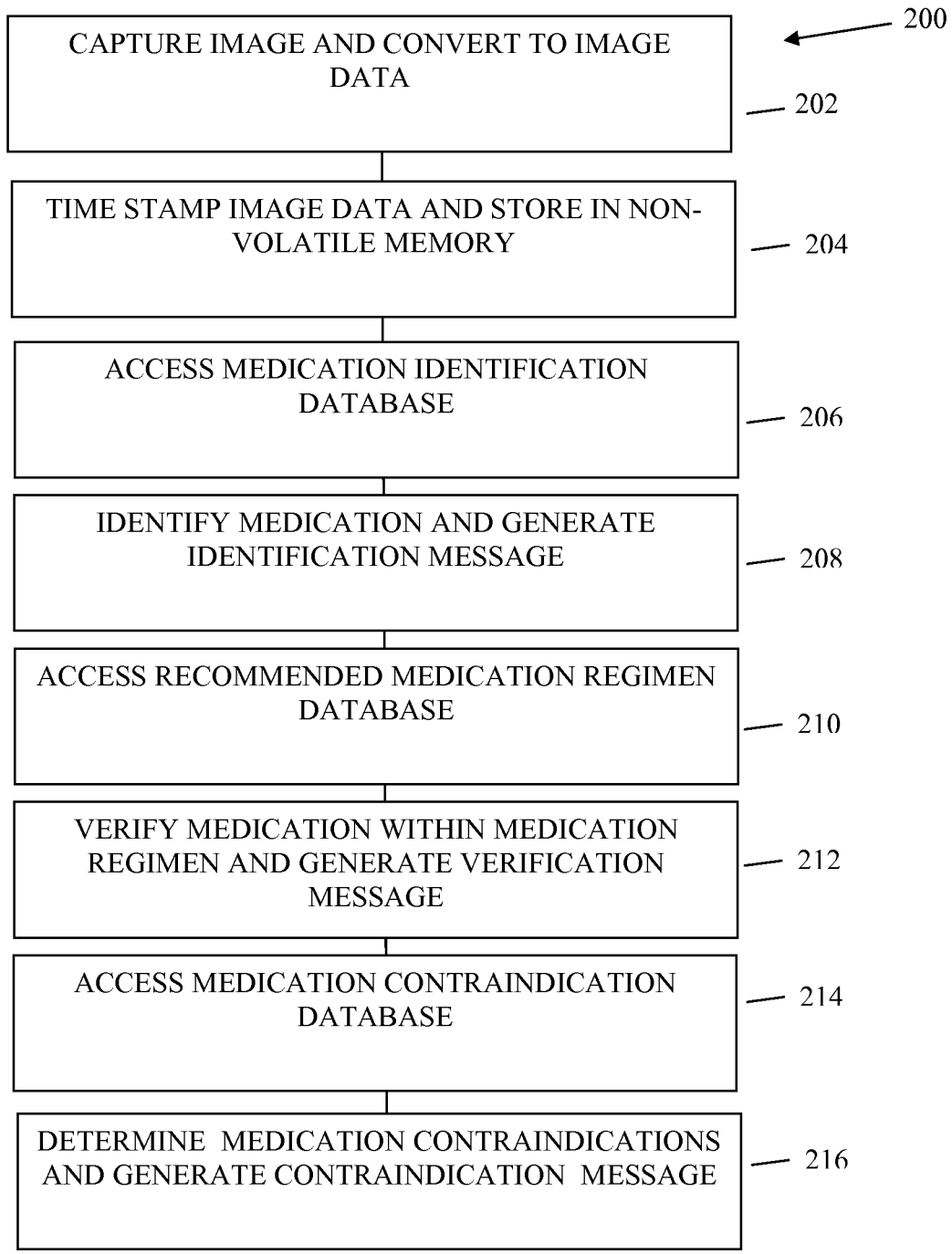
FIG. 2 is a block diagram illustrating a particular embodiment of a medication recording method.

FIG. 2 is a block diagram illustrating a particular embodiment of medication-recording process 200. In a particular embodiment, at block 202 an image of a medication to be introduced into a body may be captured and converted to image data. At block 204 the image data may be time stamped and stored. Process 200 may flow to block 206 wherein a medication-identification database may be accessed. At block 208, the medication may be identified and a message generated regarding the medication identification. Process 200 may flow to block 210 wherein a recommended-medication-regimen database may be accessed. At block 212, it may be determined whether the medication to be introduced into the body is in compliance with the recommended medication regimen and a message may be generated regarding compliance with the recommended medication regimen. Process 200 may flow to block 214 wherein a medication-contraindication database may be accessed. At block 216, it may be determined whether the medication to be introduced into the body is contraindicated and a message may be generated regarding medication contraindications.

While certain features of claimed subject matter have been illustrated as described herein, many modifications, substitutions, changes and equivalents will now occur to those skilled in the art. It is, therefore, to be understood that the appended claims are intended to cover all such embodiments and changes as fall within the spirit of claimed subject matter.

What is claimed is:

1. An apparatus, comprising:
    an imaging device configured to capture an image of a medication to be introduced into a body and a hand holding the medication;
    a time-stamp unit coupled to the imaging device and configured to generate time-stamp data in response to the imaging device capturing the image of the medication and the hand;
    a hand recognition unit coupled to the imaging device and configured to determine identification of a person whose hand appears in the image of the medication and the hand;
    a processor coupled to the imaging device, the time-stamp unit, and the hand recognition unit, the processor configured to associate image data of the image of the medication with the time-stamp data and the identified person; and
    a non-volatile memory coupled to the processor, the non-volatile memory storing the image data of the image of the medication, the time-stamp data, and the identified person,
    wherein the processor is further configured to identify the medication based on a comparison of the image data of the image of the medication with a first data set that comprises one or more medication identification parameters, the medication identification parameters comprising a color of a medication, and to determine whether the identified person is the person to receive the identified medication,
    wherein, upon determining that the identified person is the person to receive the identified medication, the processor is further configured to obtain one or more recommended-medication-regimen parameters and/or one or more parameters for determining a medication contraindication.

2. The apparatus of claim 1, further comprising:
    a second database coupled to the processor, the second database comprising at least one second data set comprising the one or more recommended-medication-regimen parameters, the processor configured to determine whether introducing the medication into the body conforms with the one or more recommended-medication-regimen parameters based at least in part on comparing the second data set with the image data of the medication and the time-stamp.

3. The apparatus of claim 2, wherein the processor is configured to communicate on a user interface a message related to whether introducing the medication into the body conforms with the one or more recommended-medication-regimen parameters.

4. The apparatus of claim 2, further comprising a transmitter coupled to the processor for communicating a message related to whether introducing the medication into the body conforms with the one or more recommended-medication-regimen parameters.

5. The apparatus of claim 1, further comprising a third database coupled to the processor, the third database comprising at least one third data set comprising the one or more parameters for determining a medication contraindication, wherein the processor is configured to determine medication contraindications based at least in part on comparing the third data set with the image data of the identified medication and the time-stamp data.

6. The apparatus of claim 5, wherein the processor is configured to communicate on a user interface a message related to whether introducing the medication into the body is contraindicated.

7. The apparatus of claim 5, further comprising a transmitter coupled to the processor for communicating a message related to whether introducing the medication into the body is contraindicated.

8. The apparatus of claim 1, further comprising a user interface, wherein the user interface is configured to generate a tactile representation of the identified medication.

9. The apparatus of claim 8, wherein the tactile representation comprises braille.

10. The apparatus of claim 1, wherein the person is a patient, a caregiver, and/or medical personnel.

11. A machine-implemented method, comprising:
    capturing an image of a medication to be introduced into a body and a hand holding the medication;
    determining identification of a person whose hand appears in the image of the medication and the hand;
    converting the image of the medication to image data of the medication, the image data in a format for comparison with medication-identification data for identifying the medication;
    generating time-stamp data in response to the capturing of the image of the medication and the hand;
    associating the image data with the time-stamp data and the identified person;
    storing the image data, the time-stamp data, and the identified person;
    accessing a first database comprising at least one first data set, the at least one first data set comprising one or more medication-identification parameters, the medication identification parameters comprising a color of a medication;
    comparing the at least one first data set with the image data of the medication;
    identifying the medication based on the comparison of the at least one first data set with the image data of the medication;
    determining whether the identified person is the person to receive the identified medication; and
    obtaining one or more recommended-medication-regimen parameters and/or one or more medication-contraindication parameters upon determining that the identified person is the person to receive the identified medication.

12. The method of claim 11, further comprising:
    generating a first message based at least in part on said identifying the medication.

13. The method of claim 11, further comprising:
generating medication data based at least in part on said identifying the medication;
accessing a second database comprising at least one second data set comprising the one or more recommended-medication-regimen parameters;
comparing the medication data with the at least one second data set;
comparing the time-stamp data with the at least one second data set; and
determining whether introducing the medication into the body conforms with the one or more recommended-medication-regimen parameters based at least in part on said comparing the time-stamp data with the at least one second data set.

14. The method of claim 13, further comprising:
accessing a third database comprising at least one third data set comprising the one or more medication-contraindication parameters;
comparing the medication data with the least one third data set;
comparing the time-stamp data with the least one third data set; and
determining whether introducing the medication into the body is contraindicated based at least in part on said comparing the medication data with the least one third data set or said comparing the time-stamp data with the least one third data set, or combinations thereof.

15. The method of claim 11, further comprising:
generating a second message based at least in part on determining whether introducing the medication into the body conforms with the one or more recommended-medication-regimen parameters.

16. The method of claim 11, further comprising generating, on a user interface, a tactile representation of the identified medication.

17. An apparatus, comprising:
an imaging device configured to capture an image of a medication to be introduced into a body and a hand holding the medication;
a time-stamping unit coupled to the imaging device and configured to generate time-stamp data in response to the imaging device capturing the image of the medication and the hand;
a hand recognition unit coupled to the imaging device and configured to determine identification of a person whose hand appears in the image of the medication and the hand;
a processor coupled to the imaging device, the time-stamp unit, and the hand recognition unit, the processor configured to associate image data of the image of the medication with the time-stamp data and the identified person;
a non-volatile memory coupled to the processor, the non-volatile memory storing the image data of the image of the medication, the time-stamp data, and the identified person; and
a diagnostic instrument communicatively coupled to the processor and configured to output a measurement to the processor, the diagnostic instrument comprising a blood sugar gauge, a blood pressure monitor, a heart rate monitor, a breath analyzer, or any combination thereof,
wherein the processor is further configured to identify the medication based on the image of the medication, and
wherein the processor is further configured to determine whether the identified medication is contraindicated based on the measurement outputted from the diagnostic instrument, wherein the measurement is associated with the identified person.

18. The apparatus of claim 17, wherein the processor is configured to receive from a user at the user interface an input indicating whether the user will perform and/or has performed an activity, wherein the processor is configured to identify whether the identified medication is contraindicated further based on comparing the received input with a second data set comprising behavioral parameters for determining a medication contraindication, and wherein the behavioral parameters of the second data set comprise parameters related to activities including physical activities and/or eating activities, the processor being configured to determine whether the identified medication is contraindicated based on whether the received input comprises one or more of the activities.

19. The apparatus of claim 18, wherein the behavioral parameters of the second data set comprise the parameters related to the physical activities comprise an exercise activity, a vehicle operation activity, a machinery operation activity, or any combination thereof.

20. The apparatus of claim 17, further comprising a user interface coupled to the processor, wherein the user interface is adapted to output a tactile representation of the identified medication.

21. The apparatus of claim 17, wherein the apparatus is a cell phone, and the processor is further configured to cause the cell phone to vibrate in response to determining that the identified medication is contraindicated.

* * * * *

UNITED STATES PATENT AND TRADEMARK OFFICE
Certificate

Patent No. 8,448,846 B2  Patented: May 28, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bradford H. Needham, North Plains, OR (US); and Kevin Rhodes, Beaverton, OR (US).

Signed and Sealed this First Day of October 2013.

CALLIE SHOSHO
*Supervisory Patent Examiner*
Art Unit 1787
Technology Center 1700

UNITED STATES PATENT AND TRADEMARK OFFICE
Certificate

Patent No. 8,448,846 B2                              Patented: May 28, 2013

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Bradford H. Needham, North Plains, OR (US); and Kevin Rhodes, Beaverton, OR (US).

Signed and Sealed this Twenty-ninth Day of October 2013.

<div style="text-align:right">

STEVEN S. PAIK
*Supervisory Patent Examiner*
Art Unit 2887
Technology Center 2800

</div>

UNITED STATES PATENT AND TRADEMARK OFFICE
CERTIFICATE OF CORRECTION

| | | |
|---|---|---|
| PATENT NO. | : 8,448,846 B2 | Page 1 of 1 |
| APPLICATION NO. | : 11/941959 | |
| DATED | : May 28, 2013 | |
| INVENTOR(S) | : Bradford H. Needham et al. | |

It is certified that error appears in the above-identified patent and that said Letters Patent is hereby corrected as shown below:

Title Page, Item (12)
  delete "Needhan et al."
  and insert --Needham et al.--.

Title Page, Item (75) Inventors, Line 1
  replace "Needhan"
  with --Needham--.

Signed and Sealed this
Twenty-fourth Day of March, 2015

Michelle K. Lee
*Director of the United States Patent and Trademark Office*